US009468581B2

(12) United States Patent
Kandori et al.

(10) Patent No.: US 9,468,581 B2
(45) Date of Patent: Oct. 18, 2016

(54) COMPRESSION DEPTH CALCULATION SYSTEM AND COMPRESSION DEPTH CALCULATION METHOD

(75) Inventors: Akihiko Kandori, Tokyo (JP); Kuniomi Ogata, Tokorozawa (JP); Ryuzo Kawabata, Higashiyamoto (JP); Yuko Sano, Kokubunji (JP); Takako Mizoguchi, Sayama (JP)

(73) Assignee: HITACHI, LTD., Tokyo (JP)

( * ) Notice: Subject to any disclaimer, the term of this patent is extended or adjusted under 35 U.S.C. 154(b) by 731 days.

(21) Appl. No.: 13/883,765

(22) PCT Filed: Nov. 28, 2011

(86) PCT No.: PCT/JP2011/077414
§ 371 (c)(1),
(2), (4) Date: May 7, 2013

(87) PCT Pub. No.: WO2012/073900
PCT Pub. Date: Jun. 7, 2012

(65) Prior Publication Data
US 2013/0226049 A1    Aug. 29, 2013

(30) Foreign Application Priority Data

Nov. 29, 2010  (JP) ................................. 2010-265073

(51) Int. Cl.
*A61H 31/00* (2006.01)
*A61B 5/103* (2006.01)
*A61B 5/00* (2006.01)

(52) U.S. Cl.
CPC .............. *A61H 31/00* (2013.01); *A61B 5/103* (2013.01); *A61B 5/4848* (2013.01);*A61H 31/005* (2013.01); *A61B 5/0053* (2013.01); *A61H 2201/5007* (2013.01); *A61H 2201/5023* (2013.01); *A61H 2201/5043* (2013.01);
(Continued)

(58) Field of Classification Search
CPC .............. A61H 31/00; A61H 31/005; A61H 2201/5092; A61H 2201/5084; A61H 2201/5064; A61H 2201/5058; A61H 2201/5007; A61H 2201/5071; A61H 2230/04; A61H 2205/084; A61H 2205/082; A61H 2201/16; A61H 2201/1619; A61H 2031/001; A61H 2031/002; A61H 2031/003; A61H 31/004; A61H 31/006; A61H 31/007; A61B 5/103; A61B 5/4848; A61B 5/0053; A61B 5/11; A61B 5/1121; A61B 5/1135
USPC ........................................... 601/41; 600/595
See application file for complete search history.

(56) References Cited

U.S. PATENT DOCUMENTS 6,013,041 A  *  1/2000  Leathers ................ G09B 23/28
                                                         601/107
6,125,299 A     9/2000  Groenke et al.
(Continued)

FOREIGN PATENT DOCUMENTS

| JP | 9-281125    | 10/1997 |
| JP | 2005-046609 | 2/2005  |
| JP | 2010-214122 | 9/2010  |

*Primary Examiner* — Justine Yu
*Assistant Examiner* — Tu Vo
(74) *Attorney, Agent, or Firm* — Baker Botts L.L.P.

(57) ABSTRACT

A compression depth calculation system is configured to calculate the compression depth which is a magnitude of depression of the compressed object generated by the compression and includes a measuring apparatus to be mounted on the object, and a compression depth calculating apparatus is configured to calculate the compression depth on the basis of information from the measuring apparatus. The compression depth calculation apparatus calculates a coefficient of transformation on the basis of a second-order differential waveform created for the information acquired from a magnetic sensor and acceleration information acquired from an acceleration sensor, creates a displacement waveform of a compressed portion by multiplying the acquired information by the coefficient of transformation, and calculates the compression depth on the basis of the displacement waveform.

6 Claims, 14 Drawing Sheets

(52) U.S. Cl.
CPC ............... *A61H 2201/5058* (2013.01); *A61H 2201/5061* (2013.01); *A61H 2201/5064* (2013.01); *A61H 2201/5071* (2013.01); *A61H 2201/5084* (2013.01); *A61H 2201/5092* (2013.01); *A61H 2203/04* (2013.01); *A61H 2203/0443* (2013.01); *A61H 2203/0456* (2013.01); *A61H 2205/00* (2013.01); *A61H 2205/08* (2013.01); *A61H 2205/084* (2013.01); *A61H 2230/04* (2013.01)

(56) References Cited

U.S. PATENT DOCUMENTS

| | | | |
|---|---|---|---|
| 6,306,107 | B1 | 10/2001 | Myklebust et al. |
| 6,390,996 | B1 | 5/2002 | Halperin et al. |
| 7,118,542 | B2 * | 10/2006 | Palazzolo ........... A61B 5/04012 601/41 |
| 7,220,235 | B2 * | 5/2007 | Geheb ................. A61B 5/11 600/587 |
| 7,476,206 | B2 * | 1/2009 | Palazzolo ........... A61B 5/04012 601/41 |
| 2001/0047140 | A1 | 11/2001 | Freeman |
| 2004/0082888 | A1 * | 4/2004 | Palazzolo ........... A61B 5/04012 601/41 |
| 2005/0101889 | A1 | 5/2005 | Freeman et al. |
| 2008/0146974 | A1 * | 6/2008 | Lund .................... A61H 31/00 601/41 |
| 2008/0208082 | A1 * | 8/2008 | Nysaether ............ A61B 5/11 600/595 |

* cited by examiner

FIG. 3
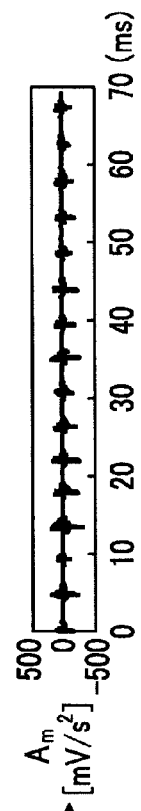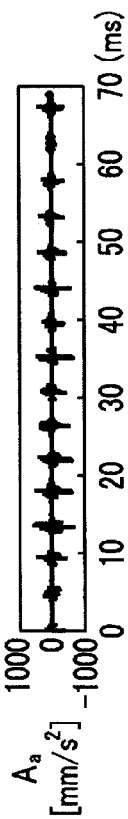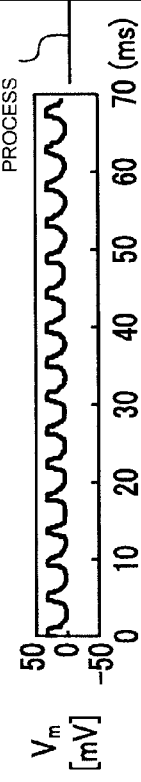

ACCELERATION [m/s$^2$]
SENSOR

MAGNETIC [V]
SENSOR

PRESSURE [N/mm$^2$]
SENSOR

DISPLACEMENT [mm]
SENSOR

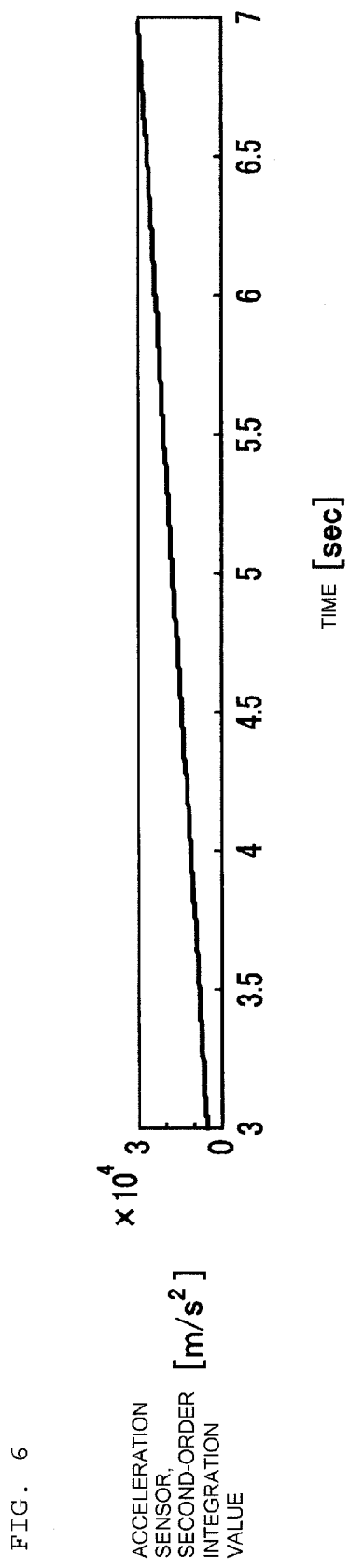

DISPLACEMENT CALCULATED ON
THE BASIS OF OUTPUT FROM
MAGNETIC SENSOR

OUTPUT FROM
DISPLACEMENT SENSOR

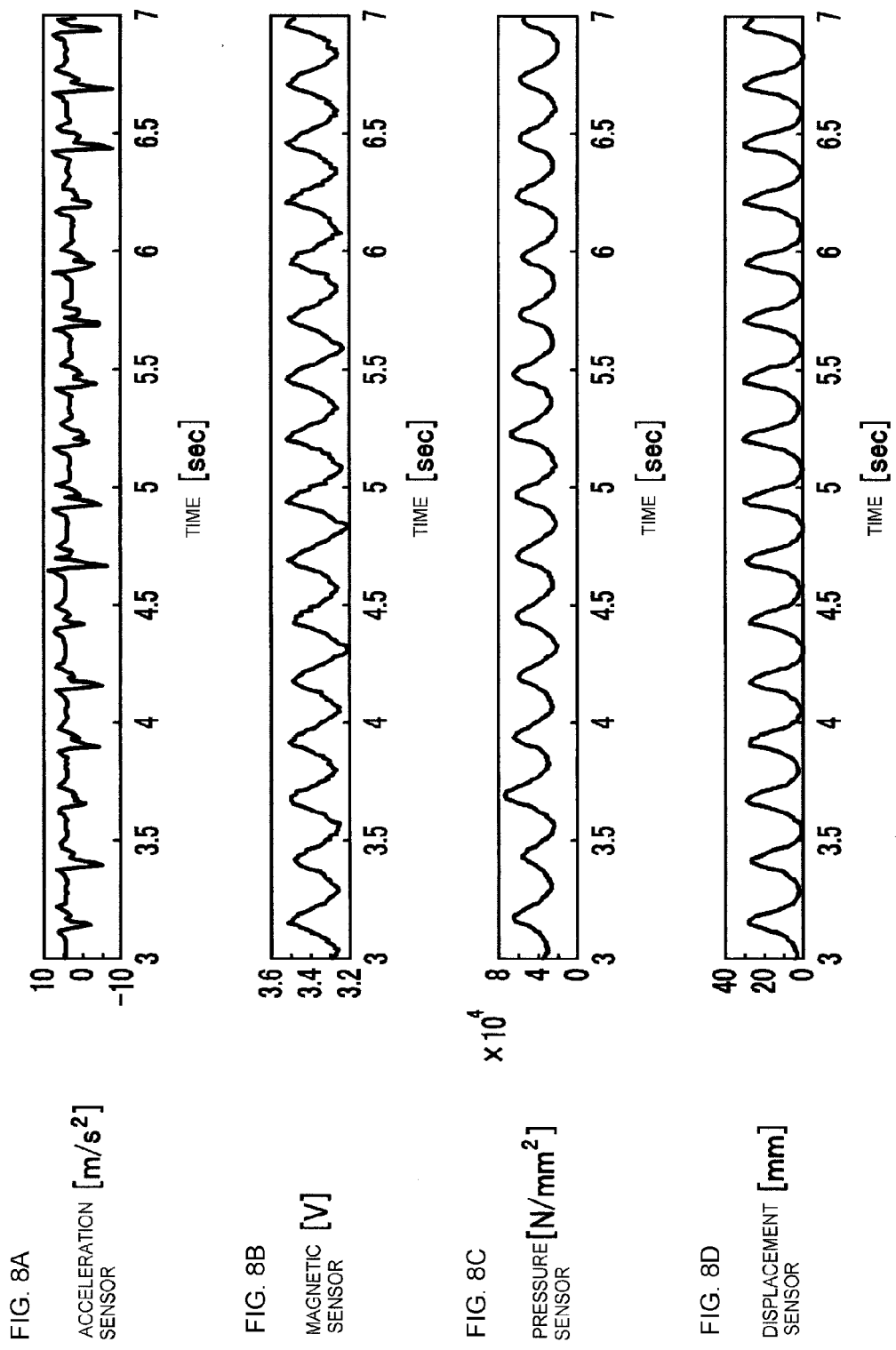

DISPLACEMENT CALCULATED ON
THE BASIS OF OUTPUT FROM
MAGNETIC SENSOR

OUTPUT FROM
DISPLACEMENT SENSOR

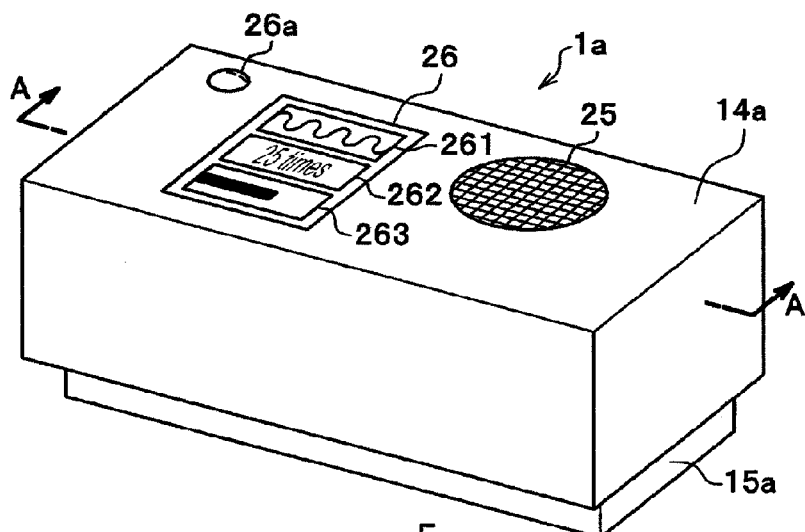
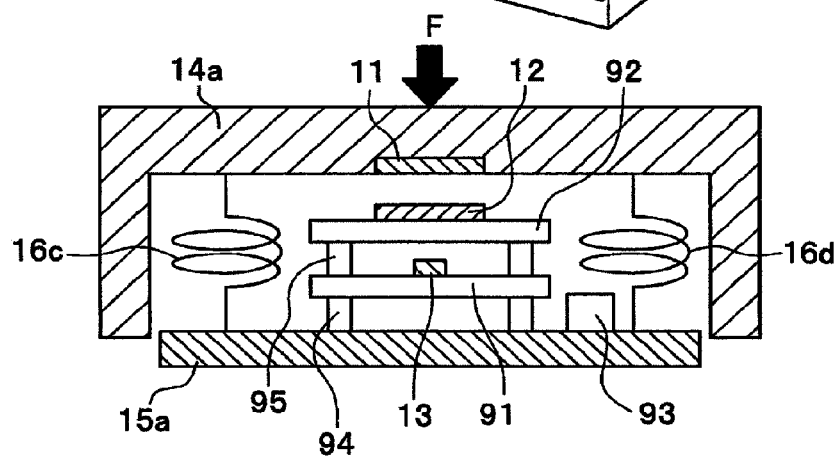
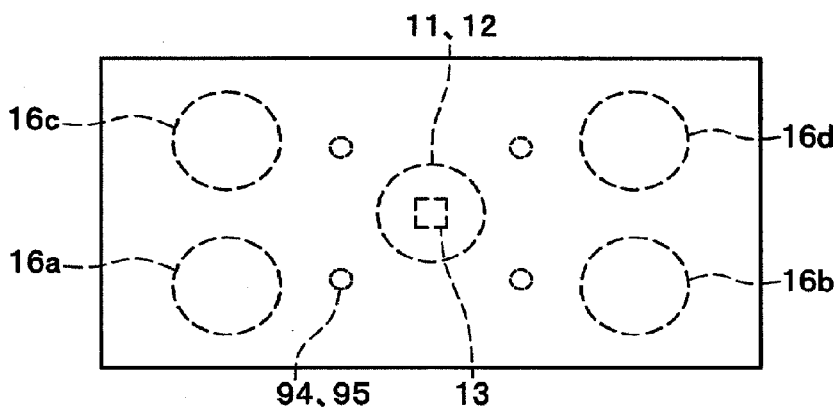

COMPRESSION DEPTH CALCULATION SYSTEM AND COMPRESSION DEPTH CALCULATION METHOD

This application is a National Stage Entry of PCT/JP2011/077414 filed Nov. 28, 2011, and claims priority from Japanese Patent Application No. 2010-265073, filed on Nov. 29, 2010, the contents of which are incorporated herein by reference in their entirety.

TECHNICAL FIELD

The present invention relates to a technology for calculating (computing) a compression depth, which is a magnitude (depth) of a depression of an object being compressed (applied with a force).

BACKGROUND ART

In recent years, importance of CPR (Cardio-Pulmonary Resuscitation) attracts attention. The term CPR means a method of resuscitating cardiopulmonary function when a sick or wounded person suffers from cardiopulmonary arrest or near-cardiopulmonary arrest. Specifically, there are artificial respiration, cardiac massage on the basis of chest compression (hereinafter, referred to simply as "chest compression"), and defibrillation of heart using AED (Automated External Defibrillator).

In order that the human brain having 10 billion or more brain cells pursue normal activities, a large amount of oxygen is required. Cessation of the oxygen supply to the brain continuing for four minutes or more causes a large number of brain cells to be destroyed, and leads to serious brain damage even though the life of the sick or injured person is maintained. Therefore, CPR which resuscitates cardiopulmonary function and causes the oxygen supply to the brain to restart as soon as possible is very important for the sick or injured person suffering from the cardiopulmonary arrest.

Here, we focus chest compression from among a plurality of detailed methods in CPR described above. There are some important points in chest compression. One of these points is that the chest is sufficiently released every time immediately after the compression by the both hands of a compressing person (the person who performs the chest compression). If this release is not sufficient, insufficient blood circulation may result. For example, in the technology of Patent Literature 1, as regards the chest compression in CPR, whether or not the chest is sufficiently released is determined by comparing outputs from a power sensor or an acceleration sensor and predetermined threshold values.

Another important point relating to the chest compression is that the compression depth is adequate. As regards the compression depth, authorities concerned in Japan and overseas provide a range from 3.8 to 5.1 cm as appropriate if the sick or injured person is adult. If the compression depth is too small, massage effects on the heart is too weak. In contrast, if the compression depth is too large, damage of breastbone or the like may result.

CITATION LIST

Patent Literature

PTL 1: JP-A-2005-46609

SUMMARY OF INVENTION

Technical Problem

However, in the related art including the technology disclosed in Patent Literature 1, the compression depth cannot be obtained with high degree of accuracy. The reason is that in the related art, the compression depth is obtained by two-order integration of an acceleration of a compression action or by one-order integration of the speed, and such methods using the integration may suffer from a large margin of error.

In this point, there is a description "the compression depth at the time of CPR may be estimated by converting an output from a power sensor into an estimated compression depth by using an estimated degree of extension" in Patent Literature 1 described above (see paragraph 0016 in Patent Literature 1). However, no detailed description is given, and hence there is no way to obtain the compression depth with high degree of accuracy.

Since the structure of the chest or the strength of the bones of human body or the like vary among different individuals, the relationship between the magnitude of the force of the chest compression and the compression depth is not constant, and the compression depth cannot be obtained with high degree of accuracy without considering such individual variability.

In view of such problems as described above, it is an object of the present invention to calculate a compression depth easily with high degree of accuracy.

Solution to Problem

In order to solve the above described problem, the present invention provides a compression depth calculation system configured to calculate a compression depth which is a magnitude of depression of a compressed object generated by compression, and the compression depth calculation system includes a measuring apparatus to be mounted on the object, and a compression depth calculating apparatus configured to calculate the compression depth on the basis of information from the measuring apparatus.

The measuring apparatus includes an acceleration sensor configured to detect the acceleration of the movement of the compressed portion of the object, and a magnetic sensor or a pressure sensor configured to output information according to the magnitude of compression with respect to the compressed portion of the object.

The compression depth calculation apparatus includes: a memory unit configured to memorize the information, a second-order differential waveform creating unit configured to create a second-order differential waveform as a waveform of an acceleration of the movement of the compressed portion by performing second-order differential on the information acquired from the magnetic sensor or the pressure sensor; a waveform comparing unit configured to compare the created second-order differential waveform and an acceleration waveform on the basis of acceleration information acquired from the acceleration sensor to output a result of comparison; and a calculating unit configured to calculate a ratio of an acceleration waveform on the basis of the acceleration information with respect to the created second-order differential waveform as a coefficient of transformation on the basis of the output result of comparison, create a displacement waveform as a waveform of displacement of the movement of the compressed portion by multiplying the acquired information by the calculated coefficient of transformation, and calculate the compression depth on the basis of the created displacement waveform.

Other solutions are given later.

Advantageous Effects of Invention

According to the present invention, the compression depth may be calculated easily with high degree of accuracy.

BRIEF DESCRIPTION OF THE DRAWINGS

FIG. 2 illustrates a configuration of a measuring apparatus and the like.

FIG. 3 (a) illustrates a magnetic sensor voltage, and in (b), (b1) illustrates a second-order differential waveform and (b2) illustrates an acceleration waveform on the basis of an output from an acceleration sensor, and (c) illustrates a chest displacement.

FIGS. 5A-5D illustrate a case where a spring having a spring constant of 0.935 kgf/mm is used, in which FIG. 5A illustrates an output from the acceleration sensor, FIG. 5B illustrates an output from the magnetic sensor, and FIG. 5C illustrates an output from a pressure sensor, and FIG. 5D illustrates an output from a displacement sensor.

FIG. 6 illustrates a second-order integration of the acceleration sensor in the case where the spring having a spring constant of 0.935 kgf/mm is used.

FIGS. 7A and 7B illustrate the case where the spring having a spring constant of 0.935 kgf/mm is used, in which FIG. 7A illustrates a displacement computed on the basis of an output from the magnetic sensor, and FIG. 7B illustrates an output from the displacement sensor.

FIGS. 8A-8D illustrate a case where a CPR training dummy is used, in which FIG. 8A illustrates an output from the acceleration sensor, FIG. 8B illustrates an output from the magnetic sensor, and FIG. 8C illustrates an output from the pressure sensor, and FIG. 8D illustrates an output from the displacement sensor.

FIGS. 10A and 10B illustrate a case where the CPR training dummy is used, in which FIG. 10A illustrates a displacement computed on the basis of an output from the magnetic sensor, and FIG. 10B illustrates an output from the displacement sensor.

FIGS. 13A-13C illustrate a modification of a measuring apparatus, in which FIG. 13A is an appearance perspective view, FIG. 13B is a cross-sectional view when viewed in the direction A in FIG. 13A, and FIG. 13C is a plan view (illustration of a voice generating unit, a display unit, and an LED is omitted).

EMBODIMENT TO CARRY OUT THE INVENTION

Figure 1:
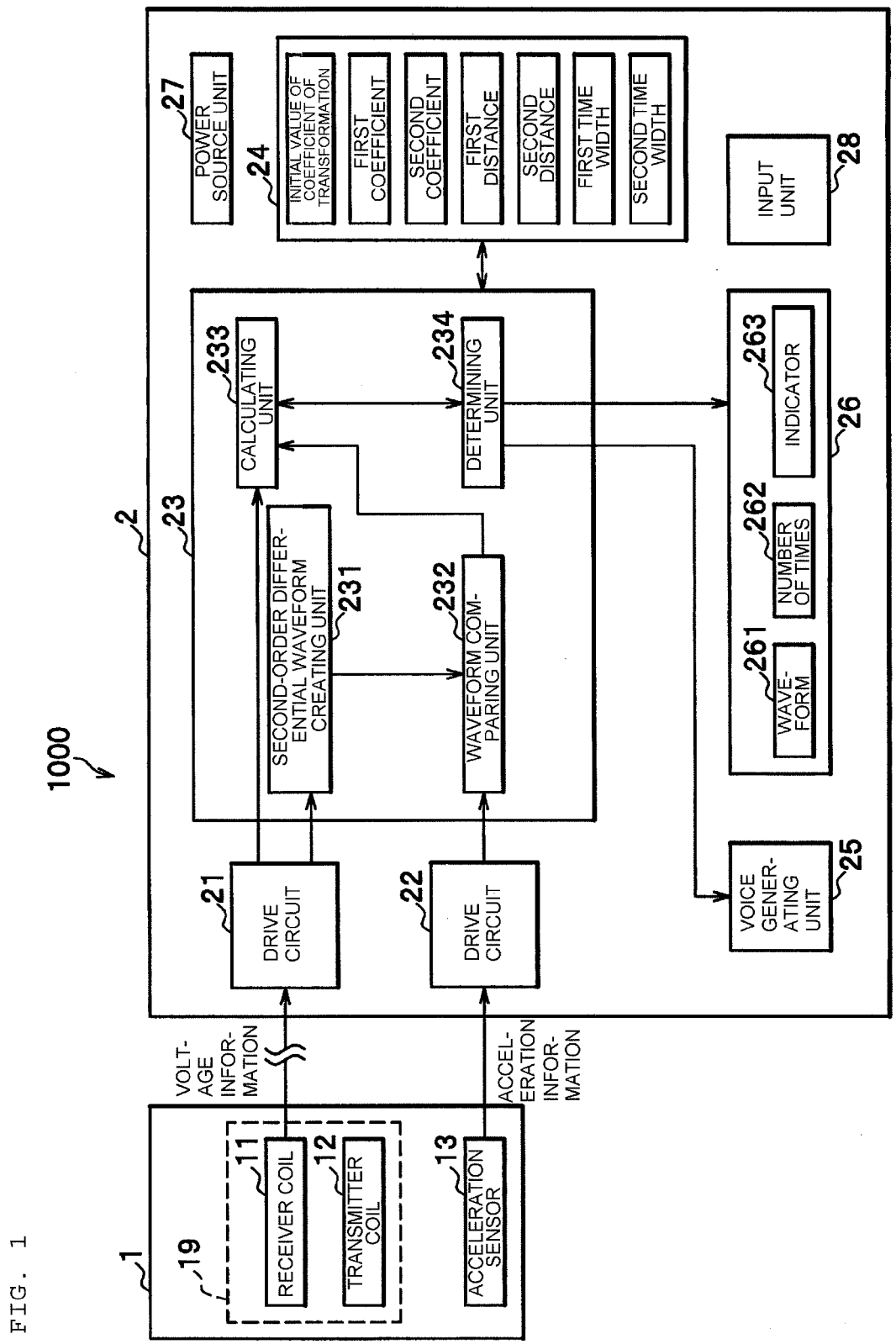
FIG. 1 illustrates a general configuration of a compression depth calculation system of an embodiment.

Referring now to the drawings as needed, modes for carrying out the present invention (hereinafter, referred to as embodiment) will be described in detail.

As illustrated in FIG. 1, a compression depth calculation system 1000 according to the embodiment includes a measuring apparatus 1 and a compression depth calculation apparatus 2.

Here, a configuration of the measuring apparatus 1 will be described with reference to FIG. 2 as well. The measuring apparatus 1 includes a receiver coil 11 (magnetic field sensing means), a transmitter coil 12 (magnetic field generating means), an acceleration sensor 13, a movable portion 14, a fixed portion 15, and a spring 16 (resilient member). The receiver coil 11 and the transmitter coil 12 are intensively referred to as a magnetic sensor 19.

The transmitter coil 12 and the acceleration sensor 13 are arranged on the fixed portion 15. The fixed portion 15 is fixed to a body B of a sick or injured person. The method of fixing contemplated is a method using a double-faced adhesive tape, for example. Here, the body B has a spring-like property and a damper-like property. However, since the spring-like property is dominant, the body B is considered to be approximately a spring 17 having a spring constant of K1.

The receiver coil 11 is arranged on the movable portion 14 so as to face the transmitter coil 12. The spring 16 having a spring constant of K2 is arranged between the movable portion 14 and the fixed portion 15. The spring 16 is selected so that a relationship of K2>K1 is satisfied. Otherwise, when a compression force F is applied to the movable portion 14 (see FIG. 2), the spring 16 is contracted to the shortest length, which limits a range of motion, whereby the function as the magnetic sensor 19 is impaired.

A distance D between the movable portion 14 and the fixed portion 15 is preferably on the order of 2 mm, for example. The following expression (1) and the expression (2) are satisfied;

$$F \approx K1 \times X1 \qquad \text{expression (1)}$$

$$F \approx K2 \times X2 \qquad \text{expression (2)}$$

where X2 is the amount of contraction of the spring 16 when the compression force F is applied to the movable portion 14, and X1 is the amount of contraction of the spring 17. If the distance D is approximately 2 mm, X2 preferably becomes approximately 0.5 mm.

Subsequently, operations of the magnetic sensor 19 and the peripheral components will be described with reference to FIG. 2. First of all, an AC oscillation source 31 generates an AC voltage having a specific frequency (for example, 20 kHz). The AC voltage is converted to an AC current having a specific frequency by an amplifier 32, and the converted AC current flows to the transmitter coil 12. A magnetic field generated by the AC current flowing in the transmitter coil 12 generates an induced electromotive force in the receiver coil 11.

The AC current generated in the receiver coil 11 by an induced electromotive force (the frequency is the same as the frequency of the AC voltage generated by the AC oscillation source 31) is amplified by a preamplifier 33, and a signal after the amplification is input to a detector circuit 34. In the detector circuit 34, the above-described signal after the amplification is detected by a specific frequency or a double frequency generated by the AC oscillation source 31. Therefore, an output from the AC oscillation source 31 is introduced into a reference signal input terminal of the detector circuit 34 as a reference signal 35. It is also possible to employ a full-wave rectifier circuit instead of the detector circuit 34 and the reference signal 35 to achieve the operation on the basis of the circuit, and the configuration of the full-wave rectifier circuit helps the realization of reduction in size and cost. Voltage information (output signal) from the detector circuit 34 (or the full-wave rectifier circuit) passes through a low-pass filter 36, and is introduced to a drive circuit 21 (see FIG. 1) of the compression depth calculation apparatus 2.

Figure 4:
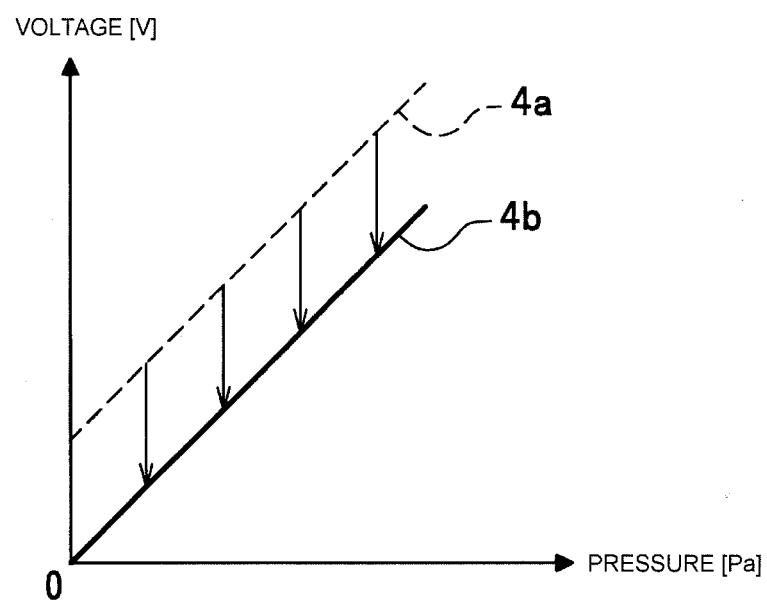
FIG. 4 illustrates a relationship between an output voltage on the side of a receiver coil and a pressure applied by compression.
Figure 5A:
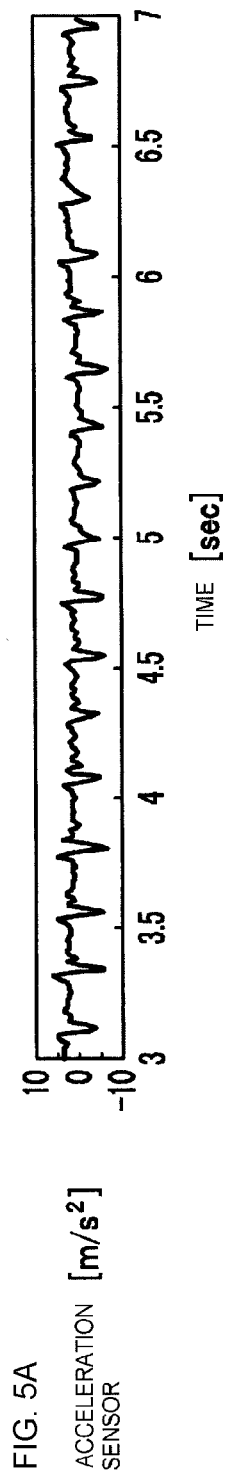
Figure 5B:
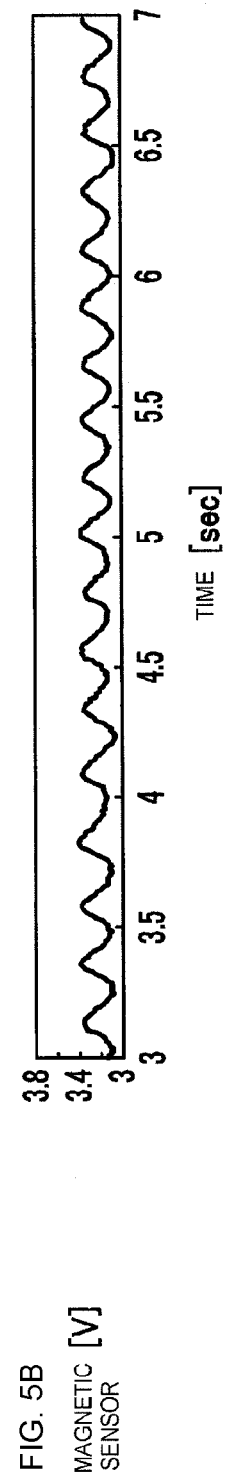
Figure 5C:
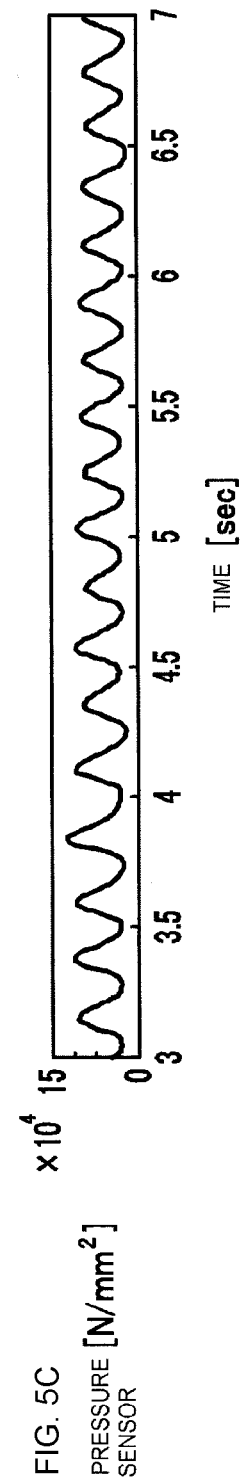
Figure 5D:
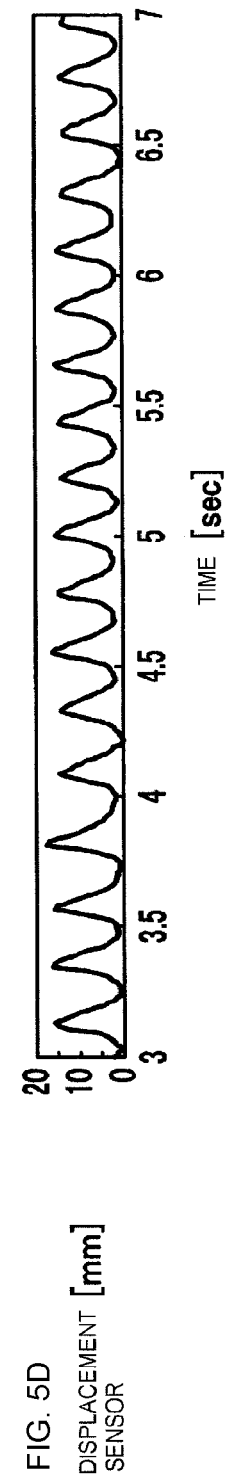

The relationship between a pressure (force F) applied to the movable portion 14 and the magnitude of the voltage expressed by the output signal introduced from the low-pass filter 36 to the drive circuit 21 is as illustrated by a line 4a (broken line) in FIG. 4. The strength of the magnetic field has a characteristic of attenuating at a rate of square of the distance. However, the reason why the line 4a extends linearly is that the spring constant K2 of the spring 16 is large, and the amount of contraction of the spring 16 with respect to the pressure to the movable portion 14 is small, and hence this characteristic may be treated as the linear characteristic. By correcting the line 4a to a line 4b (solid line) so that the voltage becomes zero when the pressure is zero, the relationship between the pressure and the voltage may have a proportional relationship passing through an original point. This correction may be performed by a processing unit 23 described later, for example.

Referring back to FIG. 1, the compression depth calculation apparatus 2 will be described below. The compression depth calculation apparatus 2 is a computer apparatus and includes the drive circuits 21, 22, the processing unit 23, a memory unit 24, a voice generating unit 25, a display unit 26, a power source unit 27, and an input unit 28.

In the drive circuit 21, voltage information received from the receiver coil 11 of the measuring apparatus 1 via the low-pass filter 36 (see FIG. 2) or the like is transmitted to the processing unit 23.

In the drive circuit 22, acceleration information received from the acceleration sensor 13 of the measuring apparatus 1 is converted into a voltage, and is transmitted to the processing unit 23.

The processing unit 23 is realized by, for example, a CPU (Central Processing Unit), and includes a second-order differential waveform creating unit 231, a waveform comparing unit 232, a calculating unit 233, and a determining unit 234. Hereinafter, the processes of these units will be described with reference also to FIG. 3, FIG. 5, and FIG. 6.

As illustrated in FIG. 5, in the case where the spring having a spring constant of 0.935 kgf/mm is used, an output from the acceleration sensor 13 becomes as illustrated in (a), an output from the magnetic sensor 19 becomes as illustrated in (b), an output when a pressure sensor (not illustrated) is used instead of the magnetic sensor 19 becomes as illustrated in (c), an output (the true value (correct value) of displacement) from a displacement sensor (not illustrated) such as a laser sensor as a reference becomes as illustrated in (d).

Here, the target is to obtain information as close as possible to the information illustrated in (d) by using at least one of items of information of the outputs illustrated in (a), (b), and (c). In other words, as it is very difficult to measure the compression depth in a case where the chest compression is performed for a sick or injured person suffering from cardiopulmonary arrest or near-cardiopulmonary arrest by using the displacement sensor such as a laser sensor, it is desired to obtain the compression depth with high degree of accuracy by using the information of the outputs from the acceleration sensor 13, the magnetic sensor 19, and the pressure sensor instead. For example, as is performed in the related art, if the output from the acceleration sensor 13 is subjected to a second-order integration, the error of the second-order integration value is increased with time as illustrated in FIG. 6, and hence it is off from practical use.

In contrast, in FIG. 5, the waveform of the output from the magnetic sensor 19 illustrated in (b) is similar to the waveform of the output from the displacement sensor illustrated in (d). Therefore, by multiplying the waveform of the output from the magnetic sensor 19 illustrated in (b) by a predetermined coefficient of transformation, the waveform of the output from the magnetic sensor 19 may be bordered upon the waveform of the output from the displacement sensor illustrated in (d). The waveform of the output from the pressure sensor illustrated in (c) is also the same.

In order to obtain the above-described coefficient of transformation, the second-order differential waveform creating unit 231 creates a second-order differential waveform on the basis of the voltage information obtained from the drive circuit 21. Specifically, a second-order differential waveform illustrated in (b1) of (b) is created by performing second-order differential process on the output voltage of the magnetic sensor 19 illustrated in (a) as illustrated in FIG. 3.

The waveform comparing unit 232 compares the second-order differential waveform illustrated in (b1) in FIG. 3 and an acceleration waveform (the same as the waveform illustrated in FIG. 5($a$)) on the basis of an output from the acceleration sensor 13 illustrated in (b2).

Referring back to FIG. 1, the calculating unit 233 performs a variety of calculations, and the determining unit 234 performs a variety of determinations. The detailed description thereof will be given later in conjunction with the description of flowcharts in FIG. 11 and FIG. 12.

The memory unit 24 is a unit for memorizing various items of information and, for example, is realized by a RAM (Random Access Memory), a ROM (Read Only Memory), and an HDD (Hard Disk Drive), and so on.

An initial value of the coefficient of transformation in the information memorized therein is an initial value of the coefficient of transformation used until an adequate coefficient of transformation is calculated, and is obtained and input in advance by a user on the basis of experiment or the like.

A first coefficient and a second coefficient are a lower limit value and an upper limit value in a range of adequate coefficient of transformation values respectively, and are obtained through an experiment or the like and are input in advance by a user.

A first distance and a second distance are a lower limit value and an upper limit value in, a range of adequate compression depth values respectively, and are input in advance by the user. For example, the first distance may be set to "3.8 cm" and the second distance may be set to "5.1 cm".

A first time width and a second time width are a lower limit value and an upper limit value in a range of an adequate interval (see FIG. 3($c$)) respectively, and are obtained through an experiment or the like and are input in advance by the user.

The voice generating unit 25 is a unit for generating a voice and is realized by a speaker or the like, for example.

The display unit 26 is a unit for a variety of displays and is realized by, for example, an LCD (Liquid Crystal Display) or a CRT (Cathode Ray Tube) Display. A waveform 261, a number of times 262, an indicator 263, and the like are displayed on the display unit 26. The waveform 261 indicates a state of a change of the compression depth with time. The number of times 262 indicates the number of times of compression. The indicator 263 indicates the magnitude of compression depth.

The power source unit 27 is a power source supply unit in the compression depth calculation apparatus 2.

The input unit 28 is a unit operated by the user for inputting a variety of items of information and, for example, is realized by a keyboard, a mouse, or the like.

Figure 7A:
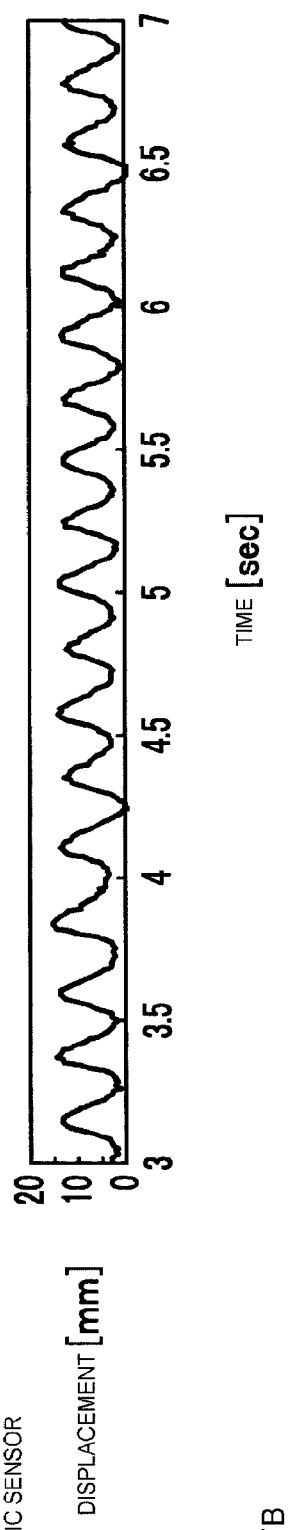
Figure 7B:
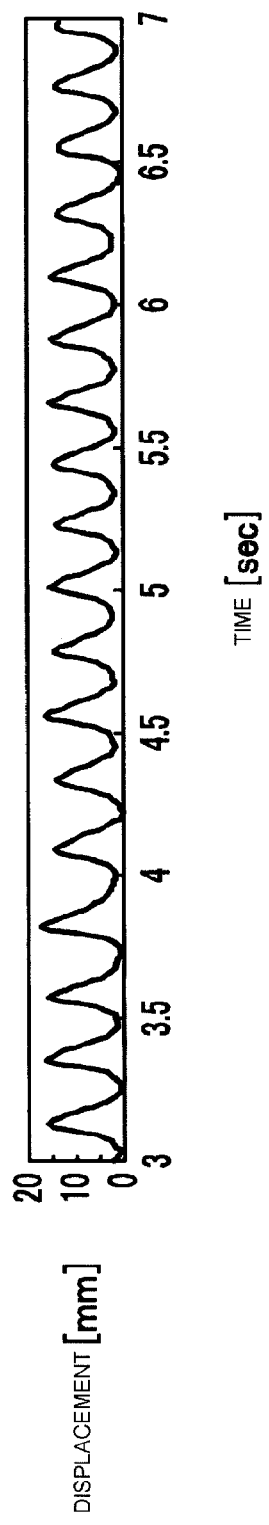
Figure 9:
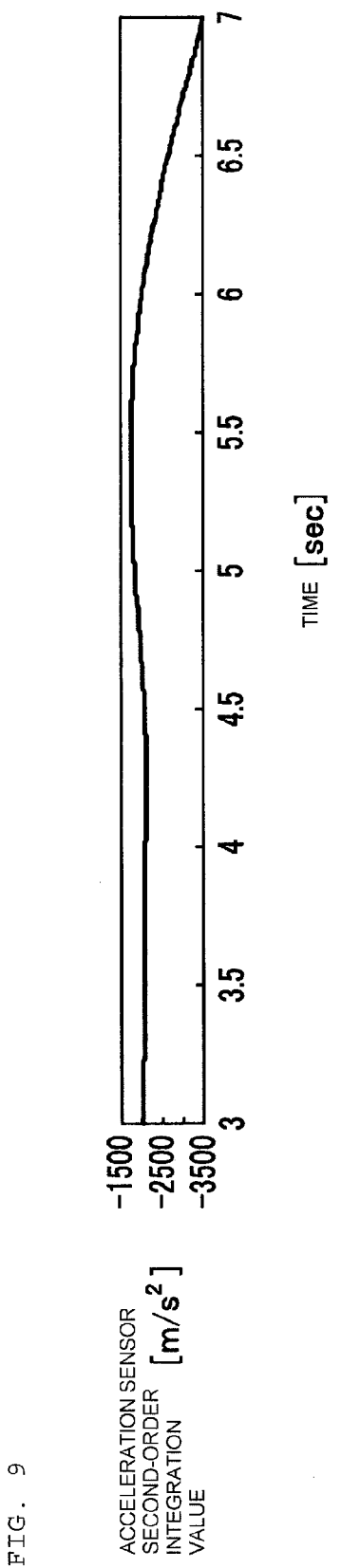
FIG. 9 illustrates a second-order integration of the acceleration sensor in a case where a CPR training dummy is used.
Figure 10A:
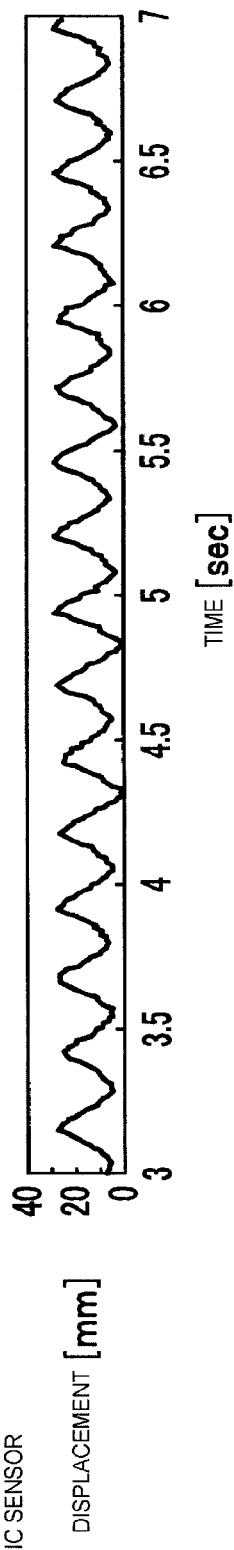
Figure 10B:
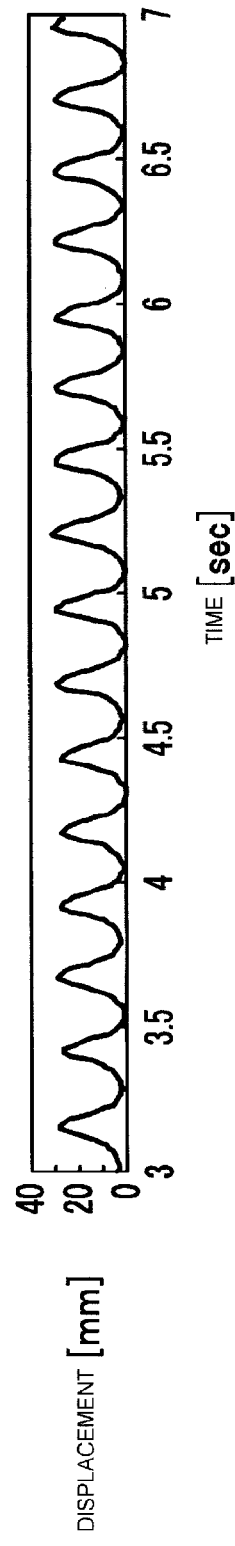

FIG. 8 to FIG. 10 are the same as FIG. 5 to FIG. 7 except that a CPR training dummy is used instead of the spring. In other words, as illustrated in FIG. 8, the waveform of the output from the magnetic sensor 19 illustrated in (b) is very similar to the waveform of the output from the displacement sensor illustrated in (d). As illustrated in FIG. 9, if the output from the acceleration sensor 13 is subjected to a second-order integration, the error of the second-order integration value is increased with time, and hence it is off from practical use. As illustrated in FIG. 10, the (displacement) waveform calculated on the basis of the output from the magnetic sensor 19 illustrated in (a) is similar to the displacement indicated by the output (the true value of displacement) from the displacement sensor illustrated in (b). Other detailed descriptions are omitted.

Figure 11:
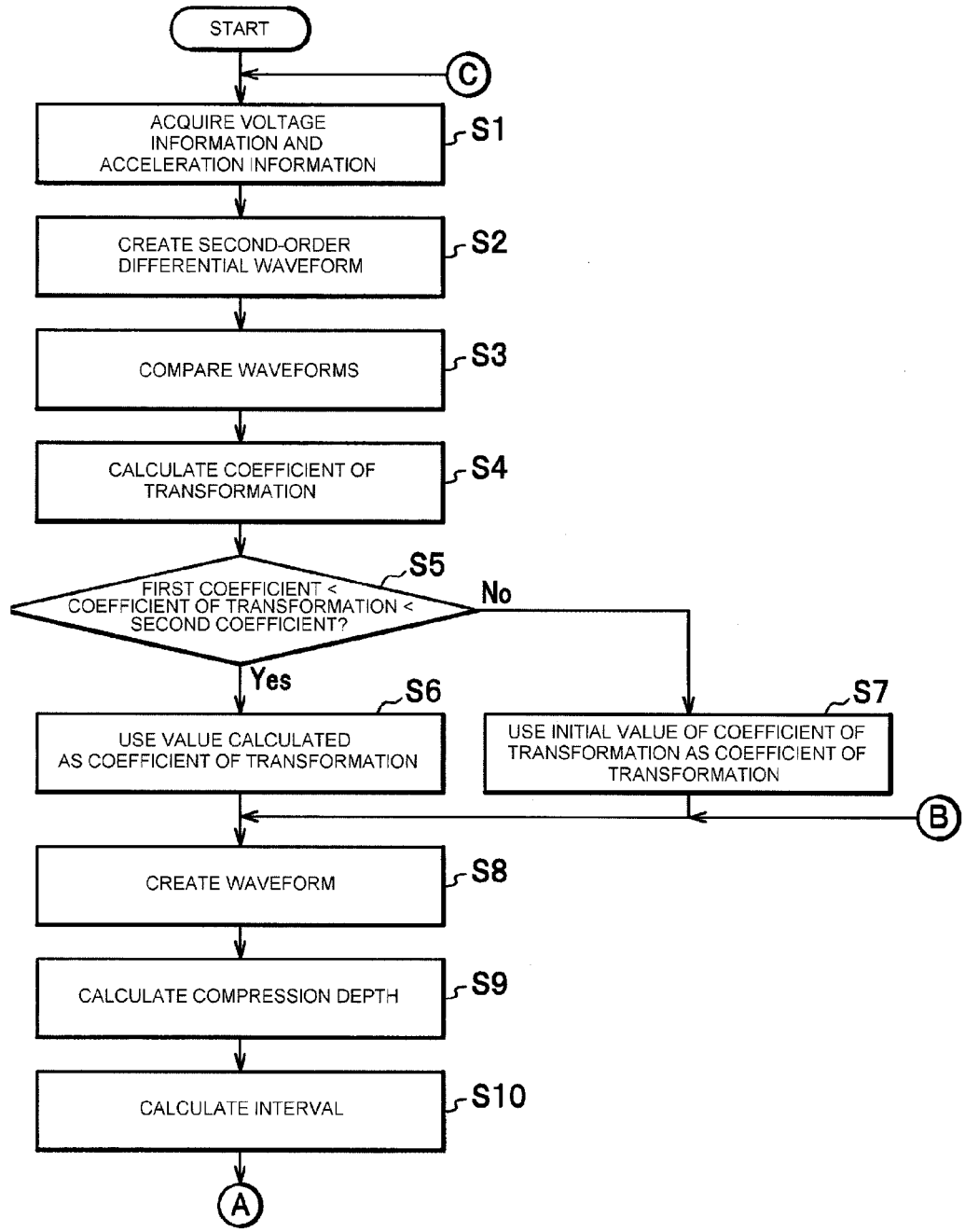
FIG. 11 is a flowchart illustrating a flow of a process performed by the compression depth calculation apparatus.
Figure 12:
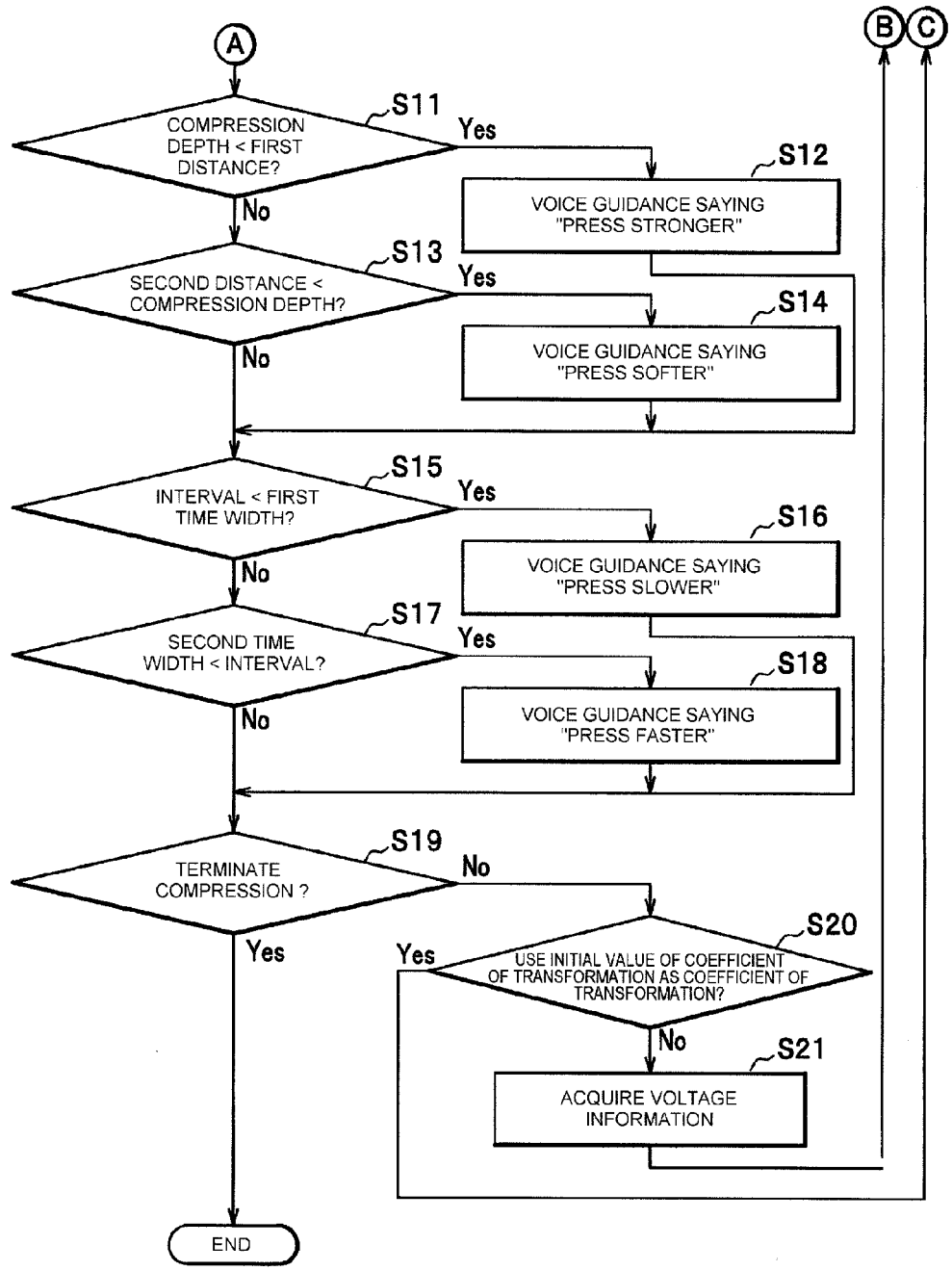
FIG. 12 is a flowchart illustrating a flow of the process performed by the compression depth calculation apparatus.

Subsequently, the process of the compression depth calculation apparatus 2 will be described with reference to the flowcharts in FIG. 11 and FIG. 12 (see other drawings as needed).

First of all, the drive circuit 21 acquires voltage information on the basis of the output from the receiver coil 11 from the low-pass filter 36, and the drive circuit 22 acquires acceleration information from the acceleration sensor 13 (Step S1).

Subsequently, the second-order differential waveform creating unit 231 creates a second-order differential waveform (see FIG. 3(b) (b1)) from the voltage information on the basis of the output from the receiver coil 11 (Step S2).

Subsequently, the waveform comparing unit 232 compares the two-order differential waveform (see FIG. 3(b) (b1)) and the acceleration waveform (see FIG. 3(b)(b2)) on the basis of the acceleration sensor 13 (Step S3).

The output from the acceleration sensor 13 includes a DC component (offset) by a gravitational force field (acceleration 1G (gravity)). In contrast, the second-order differential waveform of the output from the magnetic sensor 19 does not include such an offset. Therefore, at the time of the comparison in Step S3, in order to eliminate (or reduce) the error caused by the offset, for example, it is preferred to perform (1) an output from the acceleration sensor 13 is caused to pass through a high-pass filter so as to remove the offset, or (2) an average value of the offset with respect to the output from the acceleration sensor 13 is calculated and subtracted. Such an error may be reduced also by causing the both data to pass through the same low-pass filter having a lowered cut-off frequency (for example, a cut-off frequency of approximately 30 Hz).

Subsequently, the calculating unit 233 calculates the coefficient of transformation on the basis of the result of comparison in Step S3 (Step S4). Specifically, for example, a coefficient of transformation α may be calculated by using the following expression (3) (see FIG. 3(b)). Here, reference sign Am denotes a second-order differential waveform, and reference sign Aa denotes an acceleration (sensor) waveform. Reference sign t denotes a certain time width, and α is a ratio of integration values within a certain time range. In other words, the coefficient of transformation α is a ratio of the magnitude of the acceleration waveform (see FIG. 3(b) (b2)) on the basis of the acceleration sensor 13 with respect to the magnitude of the two-order differential waveform (see FIG. 3(b) (b1)). Therefore, the ratio of the magnitude may be calculated by a ratio such as amplitude or a power of signal other than the expression (3).

[Math. 1]

$$\alpha = \sqrt{\frac{\sum_t A_a^2}{\sum_t A_m^2}} \quad \text{expression (3)}$$

Subsequently, the determining unit 234 determines whether or not the coefficient of transformation α calculated in Step S4 satisfies the following inequality expression (4) (Step S5) and, if satisfied (Yes), the calculated value is used as the coefficient of transformation α in the following calculation (Step S6) and, if not satisfied (No), the initial value of the coefficient of transformation memorized in the memory unit 24 is used as the coefficient of transformation α in the following calculation (Step S7).

First Coefficient<Coefficient of transformation
α<Second Coefficient         expression (4).

Subsequently, the calculating unit 233 creates a waveform by using the output waveform from the magnetic sensor 19 and the coefficient of transformation α. Specifically, as illustrated in FIG. 3, a waveform Dm is created on the basis of the following expression (5) by using a waveform (Vm) and the coefficient of transformation α illustrated in (a) (Step S8).

$$Dm = \alpha \cdot Vm \quad \text{expression (5)}$$

Here, referring to FIG. 7, the fact that the waveform created in Step S8 is highly accurate will be described. As illustrated in FIG. 7, it is understood that the (displacement) waveform created in Step S8 illustrated in (a) is similar to the displacement indicated by the output (the true value of displacement) from the displacement sensor illustrated in (b), and the waveform crated in Step 8 is highly accurate.

Subsequently, returning back to FIG. 11, the calculating unit 233 calculates the compression depth and an interval on the basis of the waveform Dm created in Step S8 (Steps S9, 10). This calculation may be realized by the method of the related art.

Subsequently, the determining unit 234 references the memory unit 24, determines whether or not the compression depth calculated in Step S9 is smaller than the above-described first distance (Step S11) and, if smaller (Yes), issues an instruction to the voice generating unit 25 to generate a voice guidance saying "Press Stronger" (Step S12), and goes to Step S15 and, if not smaller (No), goes to Step S13.

In Step S13, the determining unit 234 references the memory unit 24, determines whether or not the compression depth calculated in Step S9 is larger than the above-described second distance and, if larger (Yes), issues an instruction to the voice generating unit 25 to generate a voice guidance saying "Press Softer" (Step S14), and goes to Step S15 and, if not larger (No), goes to Step S15.

In Step S15, the determining unit 234 references the memory unit 24, determines whether or not the interval calculated in Step S10 is smaller than the first time width and, if smaller (Yes), issues an instruction to the voice generating unit 25 to generate a voice guidance saying "Press Slower" (Step S16), and goes to Step S19 and, if not smaller (No), goes to Step S17.

In Step S17, the determining unit 234 references the memory unit 24, determines whether or not the interval calculated in Step S10 is larger than the second time width and, if larger (Yes), issues an instruction to the voice generating unit 25 to generate a voice guidance saying "Press Faster" (Step S18), and goes to Step S19 and, if not larger (No), goes to Step S19.

In Step S19, the determining unit 234 determines whether or not the compression is terminated and, if the compression is terminated (Yes), the process is ended and, if the compression is not terminated (No), goes to Step S20. In Step S19, determination of "the compression is terminated" may be made specifically when the output from the magnetic sensor 19 or the acceleration sensor 13 is not continued for a predetermined period (20 seconds, for example), for example.

In Step S20, the determining unit 234 determines whether or not the initial value of the coefficient of transformation is used as the coefficient of transformation α. If the initial value of the coefficient of transformation is not used (No in Step S20), the calculating unit 233 acquires voltage information on the basis of the magnetic sensor 19 (Step S21), and then, goes to Step S8 because calculation of the coefficient of transformation α anew is not necessary. If the initial value of the coefficient of transformation is used (Yes in Step S20), the procedure goes back to Step S1 because the calculating unit 233 needs to calculate the coefficient of transformation α.

In this manner, according to the compression depth calculation system 1000 of the embodiment, the compression depth can be calculated easily with high degree of accuracy by calculating the coefficient of transformation by comparing the second-order differential waveform created on the basis of the voltage information acquired from the magnetic sensor and the acceleration waveform on the basis of the acceleration information acquired from the acceleration sensor 13, creating the displacement waveform of the movement of the compressed portion by multiplying the above-described acquired voltage information by the coefficient of transformation, and calculating the compression depth on the basis of the displacement waveform. In particular, the accuracy may be improved significantly in comparison with the related art in which the two-order integration of the output from the acceleration sensor is performed.

If the calculated coefficient of transformation is not in the range of adequate coefficient of transformation values, the compression depth may be calculated with certain degree of accuracy specifically even in a time band in the early period of compression or the like by using the initial value of the coefficient of transformation.

If the calculated compression depth is smaller than the first distance, adequate guidance may be given to a compressing person by generating a voice guidance which encourages the compressing person to increase the strength of compression from the voice generating unit 25.

If the calculated compression depth is larger than the second distance, adequate guidance may be given to the compressing person by generating a voice guidance which encourages the compressing person to decrease the strength of compression from the voice generating unit 25.

Referring now to FIGS. 13(*a*) to (*c*), a modification of the measuring apparatus 1 will be described. In FIGS. 13(*a*) to (*c*), the same configurations as in FIG. 2 are designated by the same signs and the description is omitted as needed. In a measuring apparatus 1*a*, a battery 93 is arranged with respect to a fixed portion 15*a*, and a substrate 91 having the acceleration sensor 13 mounted thereon is mounted via four columns 94, and a base 92 having the transmitter coil 12 mounted thereon is mounted via four columns 95.

A movable portion 14*a* has a hollow rectangular parallelepiped opened only on a bottom surface, and is movably connected to the fixed portion 15 via four springs 16*a* to 16*d* (resilient members). The receiver coil 11 is arranged on the movable portion 14*a* at a position facing the transmitter coil 12. As illustrated in FIG. 13(*a*), the voice generating unit 25 as a speaker, the display unit 26 and LED (Light Emitting Diode) 26*a* are arranged on the upper surface of the movable portion 14*a*. The LED 26*a* is turned ON when a power switch (not illustrated) is ON and is turned OFF when the power switch is OFF, for example.

Figure 2:
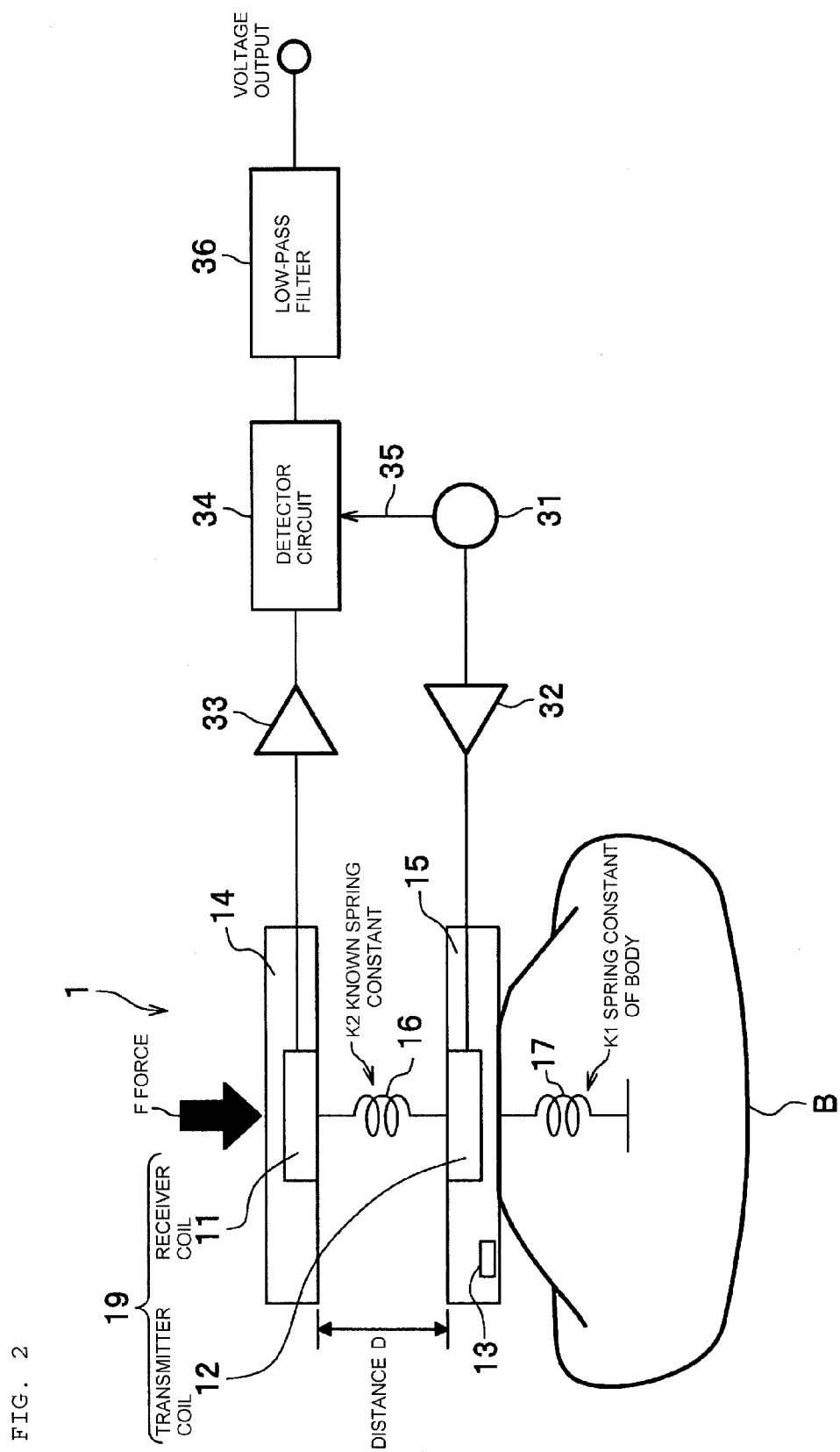

In the case of the measuring apparatus 1*a* as described above, the respective springs 16*a* to 16*d* having a resilient force approximately ¼ that of the spring 16 illustrated in FIG. 2 may be used. Also, in this manner, since the receiver coil 11, the transmitter coil 12, and the acceleration sensor 13 are arranged in a line (coaxially) in the direction of compression (force F), the force applied thereto are equivalent, and hence the sensing accuracy thereof may be improved.

By transmitting data of the waveform of the compression displacement estimated (calculated) by using the method described above (FIG. 7(*a*), FIG. 10(*a*)) to a CPR apparatus, it may be used as a reference signal which removes a noise signal in association with the chest compression which is mixed into an electrocardiographic waveform. For example, the noise signal in association with the chest compression may be removed by a method of removing noise in real time by an LMS (Least Mean Square) algorithm or the like by using a compression displacement waveform.

Subsequently, referring now to FIG. 14, another method of usage of the measuring apparatus 1 will be described. In the method described above, a compression displacement detecting method on the basis of the compression given by hands has been described. However, it is also possible to perform the compression with a compact vibrating apparatus (a piezoelectric element, a mechanical vibrating apparatus, and the like), and estimate the compression displacement detection or the hardness (spring constant). In this case, organ of human body, and industrial products (tires, for example), and food (vegetables and fruits and the like) in addition to the human body or the like are contemplated as an object O to which the compression method using a compact mechanical apparatus is applied. By calculating the compression depth of the object O, the hardness of the object may be figured out indirectly.

Figure 14A:
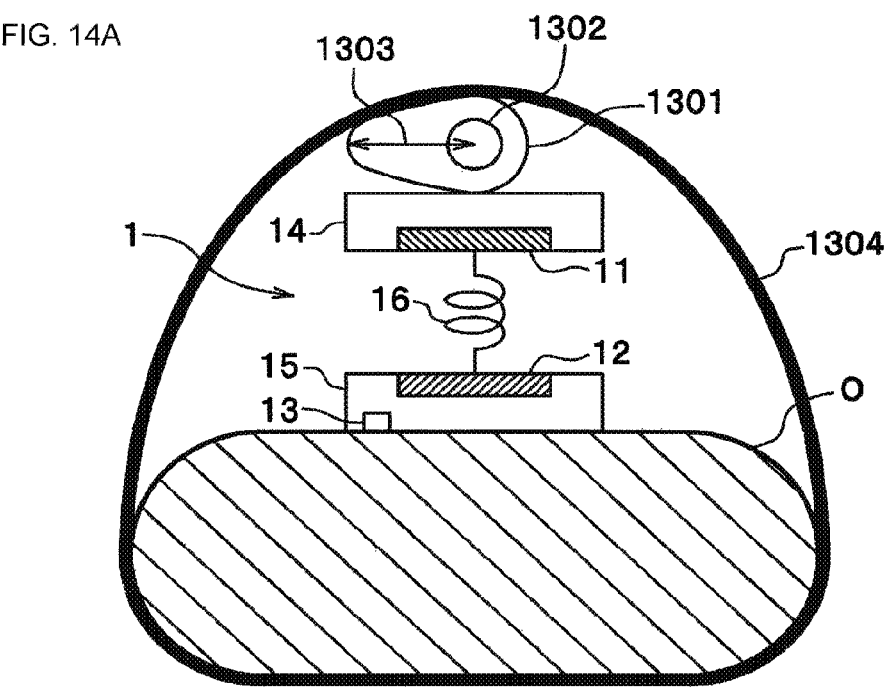
FIG. 14A schematically illustrates a state in which the compression depth of an object is calculated by using a belt and a cam, and FIG. 14B schematically illustrates a state in which the cam is rotated 90° counterclockwise from the state of FIG. 14A.
Figure 14B:
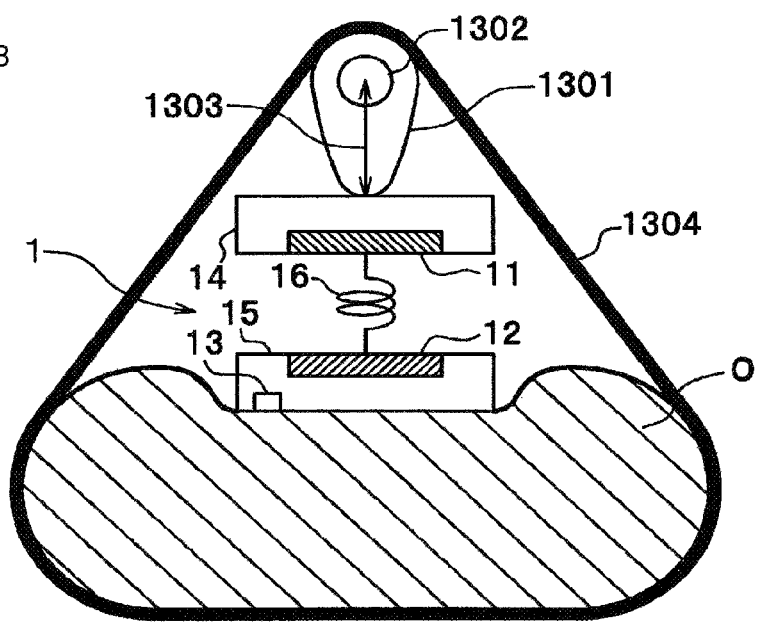

As illustrated in FIG. 14(*a*), the measuring apparatus 1 is arranged with respect to the object O as illustrated in the drawing, and a cam 1301 is arranged so as to come into contact with the movable portion 14. The cam 1301 has a shape having a long radius 1303 and rotates counterclockwise about a shaft 1302. A belt 1304 is wound around the object O and the cam 1301.

When the cam 1301 rotates 90° counterclockwise from a state in FIG. 14(*a*), s state in FIG. 14(*b*) is obtained. In the state in FIG. 14(*b*), the movable portion 14 and the fixed portion 15 get closer a little by an amount that the cam 1301 presses the movable portion 14 and the object O is depressed a little in comparison with the state in FIG. 14(*a*). The length of the belt 1304 is constant. It is also necessary to select the shape of the cam 1301 and the spring constant of the spring 16 so as to avoid the contact between the movable portion 14 and the fixed portion 15.

In this configuration, the hardness of the object O, to which the displacement sensor such as the laser sensor cannot be applied may be figured out indirectly by calculating the compression depth thereof. Specifically, this configuration may be applied to a fetal monitor configured to inspect the tightness of abdominal region of pregnant females, for example. In such a case, usage by reducing the pressing amount and combining with an ultrasonic apparatus or the like configured to confirm heart beats or the like of unborn babies is also possible.

In addition, by reducing the size as small as that a compact mechanical compressing apparatus such as the piezoelectric element and a magnetic sensor portion can be mounted on a finger tip, it may be used for an application of measurement of the harness of body during the palpation (for example, breast cancer screening or the like) or the hardness measurement of the organ during the operation. As described above, by the combination of the compression depth calculation system 1000 and the compact mechanical compression apparatus as illustrated in FIG. 1, an extremely-compact compression displacement detection or hardness (spring constant) estimation apparatus may be configured.

Although the description of the embodiment is terminated here, the mode of the present invention is not limited thereto.

For example, the pressure sensor may be used instead of the magnetic sensor, and the pressure sensor may be of any types in which a piezoelectric element is used, or a strain gauge is used.

In addition, the coefficient of transformation may be calculated further by performing the one-order differential further on the both data, calculating jerks thereof respectively, and comparing these jerks instead of comparing the second-order differential waveform obtained by performing the two-order differential on the waveform of the output of the magnetic sensor 19 and the waveform of the output from the acceleration sensor 13. Accordingly, the error caused by the DC component (offset) caused by the gravitational force field of the output from the acceleration sensor 13 may be eliminated.

Alternatively, a rectification circuit may be used instead of the detector circuit 34.

A continuous sound such as "pi, pi, . . . " sound for notifying adequate compression timings may be generated by the voice generating unit 25 in addition to the voice guidance for the compressing person.

Values such as the first coefficient, the second coefficient, the first distance, the second distance, the first time width, and the second time width may be differentiated between babies and adult, or depending on the sex, the height, the weight, and so force. In such a case, a button or the like for selecting such choices may be provided on the compression depth calculation apparatus 2. Regarding the spring 16 in the measuring apparatus 1 as well, it is also possible to prepare a plurality of types of springs 16 having different spring constants, and select one for the babies or for the adults and the like.

Although the spring 16 has been used as an example of the resilient member in the measuring apparatus 1, other resilient members such as rubber may be employed instead.

Other detailed configurations or processes may be modified as needed without departing the scope of the present invention.

REFERENCE SIGNS LIST

1, 1a measuring apparatus
2 compression depth calculation apparatus
11 receiver coil (magnetic field sensing unit)
12 transmitter coil (magnetic field generating unit)
13 acceleration sensor
14, 14a movable portion
15, 15a fixed portion
16, 16a spring (resilient member)
17 spring
19 magnetic sensor
21 drive circuit
22 drive circuit
23 processing unit
24 memory unit
25 voice generating unit
26 display unit
26a LED
27 power source unit
28 input unit
31 AC oscillation source
32 amplifier
33 preamplifier
34 detector circuit
35 reference signal
36 low-pass filter
91 substrate
92 base
93 battery
94 column
95 column
231 second-order differential waveform creating unit
232 waveform comparing unit
233 calculating unit
234 determining unit
261 waveform
262 number of times
263 indicator
1000 compression depth calculation system
1301 cam
1302 shaft
1033 long radius
B body
O object

The invention claimed is:

1. A compression depth calculation system configured to calculate a compression depth as a magnitude of a depression of a compressed object generated by compression, the compression depth calculation system comprising:
   a measuring apparatus configured to be mounted on the object, and a compression depth calculation apparatus configured to calculate the compression depth on the basis of information from the measuring apparatus, wherein
   the measuring apparatus includes:
   an acceleration sensor configured to detect an acceleration of a movement of a compressed portion of the object; and
   a magnetic sensor or a pressure sensor configured to output information according to the magnitude of compression with respect to the compressed portion of the object, and
   the compression depth calculation apparatus includes:
   a memory unit configured to memorize information,
   a second-order differential waveform creating unit configured to create a second-order differential waveform as a waveform of an acceleration of the movement of the compressed portion by performing second-order differential on the information acquired from the magnetic sensor or the pressure sensor;

a waveform comparing unit configured to compare the created second-order differential waveform and an acceleration waveform on the basis of acceleration information acquired from the acceleration sensor to output a result of comparison; and a calculating unit configured to calculate a ratio of the acceleration waveform on the basis of the acceleration information with respect to the created second-order differential waveform as a coefficient of transformation on the basis of the output result of comparison;

create a displacement waveform as a waveform of displacement of the movement of the compressed portion by multiplying the information acquired from the magnetic sensor or the pressure sensor by the calculated coefficient of transformation; and calculate the compression depth on the basis of the created displacement waveform.

2. The compression depth calculation system according to claim 1, wherein the memory unit memorizes a predetermined range of values of the coefficient of transformation input in advance and an initial value of coefficient of transformation input in advance, the compression depth calculation apparatus further includes:

a determining unit configured to determine whether or not the calculated coefficient of transformation is within the range and, if determined not to be within the range, determine to use the initial value of the coefficient of transformation as the coefficient of transformation.

3. The compression depth calculation system according to claim 1, wherein the memory unit memorizes a distance which is a predetermined lower limit value of the compression depth input in advance;

the compression depth calculation apparatus further includes a voice generating unit configured to generate a voice; and a determining unit configured to determine whether or not the calculated compression depth is smaller than the distance and, if determined to be smaller, causes the voice generating unit to generate a voice guidance that encourages a compressing person who compresses the object to increase a compression strength.

4. The compression depth calculation system according to claim 1, wherein the memory unit memorizes a distance which is a predetermined upper limit value of the compression depth input in advance;

the compression depth calculation apparatus further includes a voice generating unit configured to generate a voice; and a determining unit configured to determine whether or not the calculated compression depth is larger than the distance and, if determined to be larger, causes the voice generating unit to generate a voice guidance that encourages the compressing person who compresses the object to decrease a compression strength.

5. The compression depth calculation system according to claim 1, wherein the measuring apparatus includes:

the magnetic sensor configured to output information according to the magnitude of compression with respect to the compressed portion of the object, the magnetic sensor includes:

a fixed portion to be fixed to the compressed portion of the object;

a magnetic field generating unit configured to be arranged on the fixed portion and generate a magnetic field;

a movable portion provided at a position facing the fixed portion so as to be movable in a direction of the compression;

a magnetic field sensing unit arranged on the movable unit and configured to sense the magnetic field; and a resilient member both ends of which are mounted to the fixed portion and the movable portion respectively, and having a higher rigidity than that of the object, and the magnetic field generating unit, the magnetic field sensing unit, and the acceleration sensor arranged on the fixed portion are arranged in a line in the direction of the compression.

6. A compression depth calculation method by a compression depth calculation system configured to calculate a compression depth as a magnitude of a depression generated by compression of a compressed object, the compression depth calculation method comprising:

acquiring acceleration information according to an acceleration of a movement of a compressed portion of the object;

obtaining magnitude information according to the magnitude of compression with respect to the compressed portion of the object, creating a second-order differential waveform as a waveform of an acceleration of the movement of the compressed portion by performing second-order differential on the magnitude information, comparing the second-order differential waveform and an acceleration waveform on the basis of the acceleration information to determine comparison information, calculating a ratio of magnitude of the acceleration waveform on the basis of the acceleration information with respect to the magnitude of the created-second-order differential waveform as a coefficient of transformation on the basis of the comparison information, creating a displacement waveform as a waveform of displacement of the movement of the compressed portion by multiplying the magnitude information by the calculated coefficient of transformation; and calculating the compression depth on the basis of the created displacement waveform.

* * * * *